(12) United States Patent
Burukhin et al.

(10) Patent No.: US 9,797,878 B2
(45) Date of Patent: Oct. 24, 2017

(54) METHOD FOR DETERMINING DISTRIBUTION AND PROFILE OF A CONTAMINANT IN POROUS MEDIUM

(71) Applicant: SCHLUMBERGER TECHNOLOGY CORPORATION, Sugar Land, TX (US)

(72) Inventors: Alexander Alexandrovich Burukhin, Moscow (RU); Anna Viktorovna Zharnikova, Moscow (RU); Nikita Ilyich Ryzhikov, Moscow (RU); Dmitry Nikolaevich Mikhailov, Moscow (RU)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 0 days.

(21) Appl. No.: 14/577,257

(22) Filed: Dec. 19, 2014

(65) Prior Publication Data
US 2015/0177218 A1 Jun. 25, 2015

(30) Foreign Application Priority Data
Dec. 25, 2013 (RU) .................................. 2013157415

(51) Int. Cl.
*G01N 33/28* (2006.01)
*G01N 21/64* (2006.01)
*G01N 21/25* (2006.01)

(52) U.S. Cl.
CPC ....... *G01N 33/2823* (2013.01); *G01N 21/253* (2013.01); *G01N 21/64* (2013.01); *G01N 2201/04* (2013.01)

(58) Field of Classification Search
None
See application file for complete search history.

(56) References Cited

U.S. PATENT DOCUMENTS

2004/0185109 A1* 9/2004 Cody .................. B01F 17/0042
424/489
2012/0316259 A1* 12/2012 de Oliveira Filho .. A01N 33/04
523/122

OTHER PUBLICATIONS

Pellizzari, Linda, et al. "The use of tracers to assess drill-mud penetration depth into sandstone cores during deep drilling: method development and application." Environmental earth sciences 70.8 (2013): 3727-3738.*

(Continued)

*Primary Examiner* — Shawn Decenzo

(57) ABSTRACT

A suspension of a contaminant comprising at least one solid component and colored with at least one cationic dye is prepared. The suspension is injected through a sample of the porous medium and the sample is then split. A distribution and a profile of the contaminant in the sample is determined on the basis of a distribution and an intensity of the at least one cationic dye.

8 Claims, 4 Drawing Sheets

(56) References Cited

OTHER PUBLICATIONS

Longeron, et al, "An Integrated Experimental Approach for Evaluating Formation Damage Due to Drilling and Completion Fluids", SPE 30089, (1995) Society of Petroleum Engineers, pp. 117-131.
Jiao, et al., "Formation Damage Due to Static and Dynamic Filtration of Water-Based Muds," SPE 23823, (1992) Society of Petroleum Engineers, pp. 491-501.
Gray, et al., "Formation Damage in Sandstones Caused by Clay Dispersion and Migration", Clays and Clay Minerals (1966) vol. 14 pp. 355-366.
Nadeev, et al., "Visualization of Clay and Frozen Substances Inside Porous Rocks Using X-ray Micro-Computed Tomography," (Mar. 2013) Microscopy and Analysis, vol. 27, pp. 8-11.

\* cited by examiner

METHOD FOR DETERMINING DISTRIBUTION AND PROFILE OF A CONTAMINANT IN POROUS MEDIUM

CROSS-REFERENCE TO RELATED APPLICATION

This application claims priority to Russian Application No. 2013157415 filed Dec. 25, 2013, which is incorporated herein by reference in its entirety.

BACKGROUND

The invention relates to methods for analyzing samples of porous materials; in particular, the invention can be used for qualitative and quantitative determination of a penetration profile of drilling mud components, and for studying a deterioration of properties in a near-borehole zone of oil/gas-containing formations associated therewith.

The problem of damaging a near-borehole zone of a formation when subjected to penetrated components of a drilling mud (or a flushing fluid) is very important, especially for long horizontal boreholes, because many of them are pumped in the uncased state, i.e., without a cemented and perforated production string.

Drilling muds are complex mixtures of polymers, particles (calcium carbonate, barium sulfate having a size from hundreds of micrometers to less than one micron), clays, and other additives contained in a "carrier" fluid being "a base" of the drilling mud; water, oil, or some synthetic fluid that can act as the carrier fluid.

In the process of drilling under the influence of excessive pressure a filtrate of drilling mud as well as fine particles contained therein, polymers and other components penetrate into a near-borehole zone of a formation and cause significant reduction in the permeability thereof. In addition, an external filter cake comprised of filtered solid particles and other components of the drilling mud is formed on a wall of a borehole.

During the technological procedure of cleaning the borehole (by gradual putting into production), the external filter cake is partially broken while the penetrated components of the drilling mud are partially washed out of the near-borehole zone, and its permeability is partially restored. Nevertheless, a portion of the components remain irreversibly held in a pore space of a rock (adsorption on surfaces of pores, capture in steam restrictions, etc.) which results in an essential difference between an initial permeability and a permeability restored after carrying out the technological cleaning procedure (usually, the restored permeability is not greater than 50 to 70% of the initial permeability).

The conventional laboratory technique for checking a quality of a drilling mud is a filtration experiment for injecting a drilling mud into a core sample followed by back pumping, (i.e., displacement of the penetrated drilling mud with an initial formation fluid). (cf., Longeron D. G., Argillier J., Audibert A. An Integrated Experimental Approach for Evaluating Formation Damage Due to Drilling and Completion Fluids. SPE 30089, or Jiao D., Sharma M. M. Formation Damage Due to Static and Dynamic Filtration of Water-Based Muds. SPE 23823).

Said prior art technique allows measurement only of an integral hydraulic resistance of a core sample (a ratio of a current pressure differential across the core to a current flow rate), the change of which is caused by the growth/destruction dynamic of the external filter cake at an end face of the core and by accumulation/removal of the drilling mud components in the rock.

However, a profile and a distribution of drilling mud components as well as damaged porosity and permeability along the core sample (i.e., along a filtration axis) after pumping of the drilling mud in (or after back pumping) are important information in understanding the formation damage mechanism and to select a respective technique for increasing a wellbore productivity index (to minimize a damage of a bottomhole formation zone). The present parameters are not measured within said traditional procedure of the drilling mud quality check.

To determine said parameters, it is necessary to use additional techniques.

SUMMARY

The method makes it possible to determine a distribution and a profile of a penetrated contaminant in a porous medium with a sufficiently high accuracy and a high resolution.

In accordance with the method for determining a distribution and a profile of a contaminant in a porous medium, a suspension of the contaminant comprising at least one solid component and colored with at least one cationic dye is prepared. The prepared suspension of the colored contaminant is injected through a sample of the porous medium and then the sample is split. The distribution and the profile of the contaminant in the porous medium sample is based on a distribution and an intensity of the at least one dye.

The suspension of the colored contaminant comprising one solid component is prepared by adding one cationic dye to the suspension of the contaminant. In accordance with an embodiment of the disclosure, a suspension of the colored contaminant is prepared by adding another cationic dye to the suspension of the contaminant comprising one solid component and the suspension colored by the other cationic dye is injected through the porous medium sample.

The suspension of the colored contaminant comprising several solid components is prepared by coloring different solid components of the contaminant with different cationic dyes.

Fuchsine and/or methylene blue and/or brilliant green can be used as the cationic dyes. It is possible to use cationic dyes having special properties, for example, fluorescent dyes or dyes comprising ingredients which make it possible to determine the contaminant distribution reliably by carrying out energy-dispersive microanalysis on a scanning electron microscope.

In accordance with an embodiment, a mountain rock core can be used as the porous medium sample. At the same time, for example, bentonite or particles with a negative-charged surface, such as calcium carbonate or barium sulfate, can be used as the contaminant.

In accordance with other embodiment of the disclosure, after injecting the suspension of the colored contaminant through the mountain rock core a formation fluid is injected from an end face of the core opposite the end from which the colored contaminant suspension was injected.

In accordance with another embodiment of the disclosure, another cationic dye, different from that used to color the contaminant, is applied onto a surface of the sample.

BRIEF DESCRIPTION OF DRAWINGS

The invention is explained by the drawings where.

DETAILED DESCRIPTION

In accordance with the disclosed method, components of a penetrated contaminant, for example, a drilling mud, are contrasted by cationic dyes which are strongly held in a crystalline structure of a component and (or) on a surface thereof due to cationic exchange and (or) chemisorption.

Such traditional cationic dyes as fuchsine, methylene blue and/or brilliant green, etc., can be used as the cationic dyes. For this purpose, cationic dyes having special properties, for example, fluorescent dyes, such as rhodamine 6G can be also used when contrasting and identification can be carried out on the basis of the radiation intensity, or dyes comprising specific ingredients (for example, Alcian Blue 8GX with copper content) can be used for contrasting on the basis of an elemental composition with the use of energy-dispersive microanalysis on a scanning electron microscope when it seems impossible to determine a color contrast.

After filtration (or filtration followed by purifying), the sample is split in a direction of interest and a coloration intensity associated with a concentration of a drilling mud component penetrated in the porous material is studied.

The coloration of different solid components of the contaminant with different dyes prior to the preparation of the suspension makes it possible to study distributions and penetration profiles of each component individually.

Figure 1:
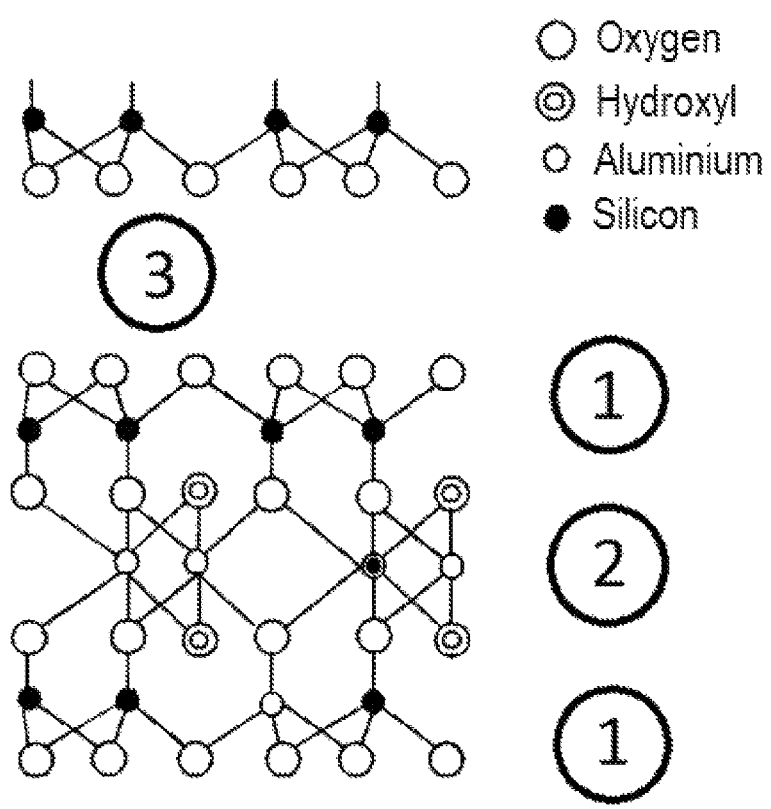
FIG. 1 shows a layered crystalline structure of montmorillonite.
Figure 2:
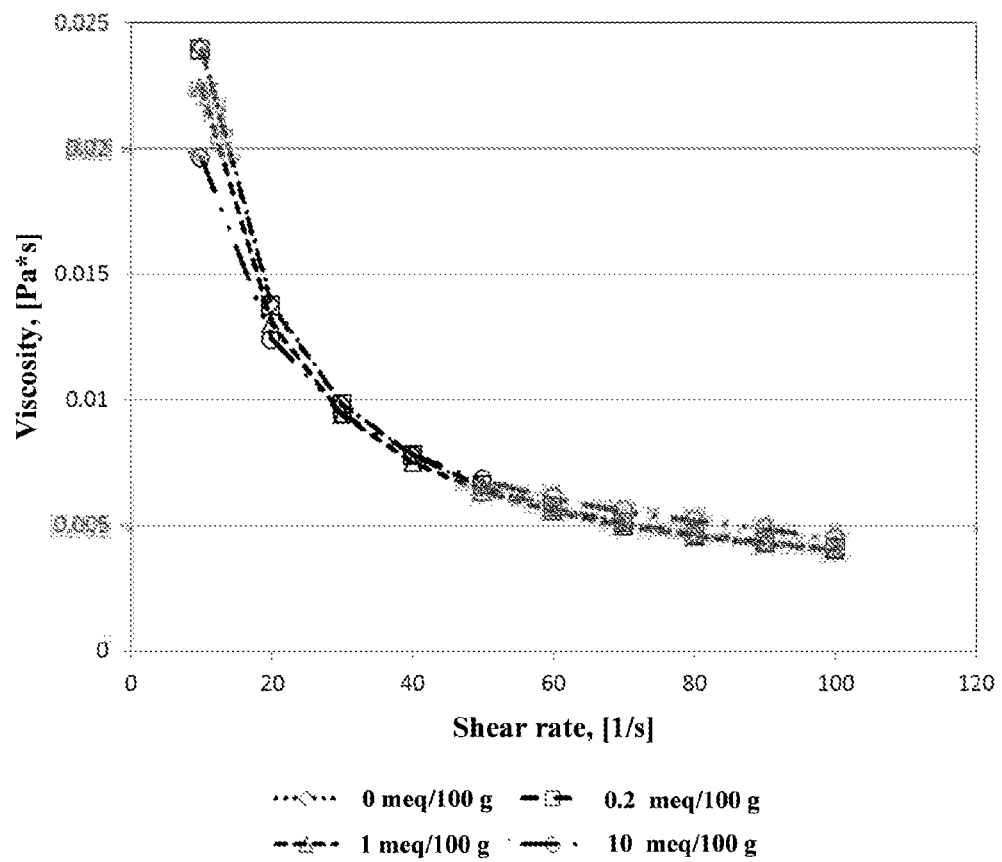
FIG. 2 shows rheological properties of pure bentonite and bentonite colored with the brilliant green dye in a concentration of from 0.2 to 10 mg-eq/100 g.

The coloration of (one or more) different solid components of the contaminant is carried out by applying a cationic dye either onto a surface (for example, onto particles of carbonates, barium sulfate or other materials carrying a negative charge on a surface) or into an interlayer space of a crystalline lattice of clayed matters having the montmorillonite structure (FIG. 1). The crystalline lattice of montmorillonite consists of tetrahedral layers (1) which surround octahedral layers (2). A space (3) filled with hydrated cations which can be substituted for other particles having a positive charge, cationic dyes in this case, is between the present structures. In case of coloring a surface, it is treated with a dye solution being the same as that added into the suspension or another, while an excess (if any) is removed by washing. In case of bentonite, a used dye quantity should be less than a cation exchange capacity of clay to provide the complete absorption of a pigment and to avoid the presence of a free dye in the fluid. The high coloration intensity of pigments allows the use of low dye concentrations and hold rheological properties of the clay slurry unchanged (FIG. 2).

In accordance with an embodiment of the disclosure, contrasting of components (for example, clayed matters) of the initial porous medium is carried out by coloring a surface of the sample with a dye different from that used to color the contaminant. This will distinguish clayed materials of the rock from bentonite added from the drilling mud during microscopic examination.

A subsequent injection of the contaminant suspensions colored with different dyes, for example, when a suspension source is switched at determined intervals between tanks containing contaminants colored with different dyes, will allow time marks to be used and to observe penetration of particles at different stages of forming the filter cake and back filtering (cleaning) the rock.

Figure 3:
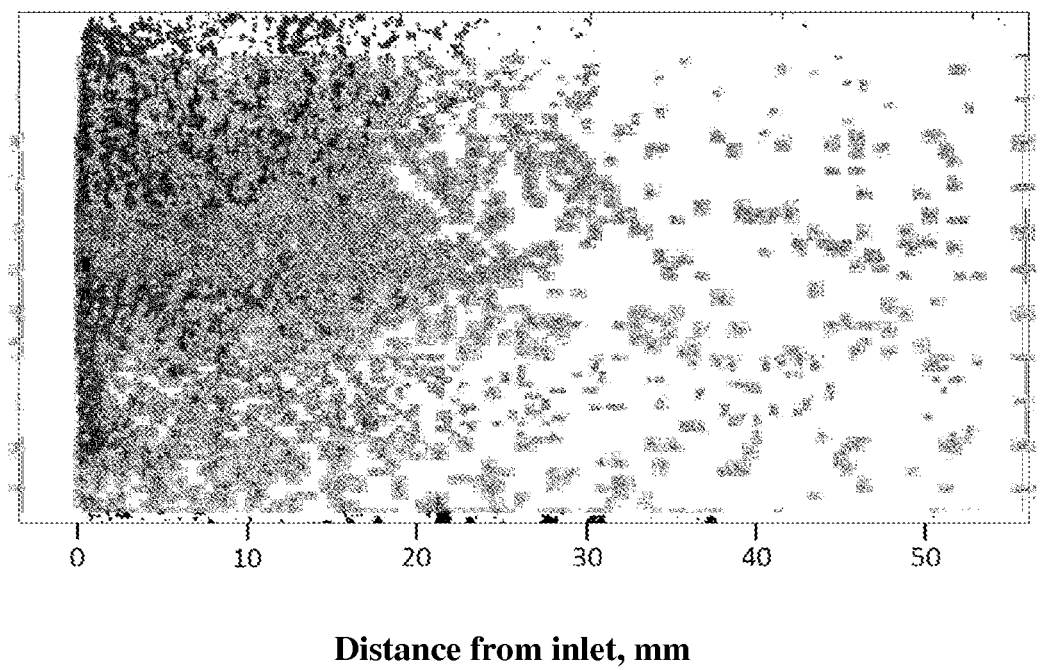
FIG. 3 shows a zone where the bentonite contaminant (a 1% slurry in a 1.8% NaCl solution) penetrates into Castlegate sandstone.
Figure 4:
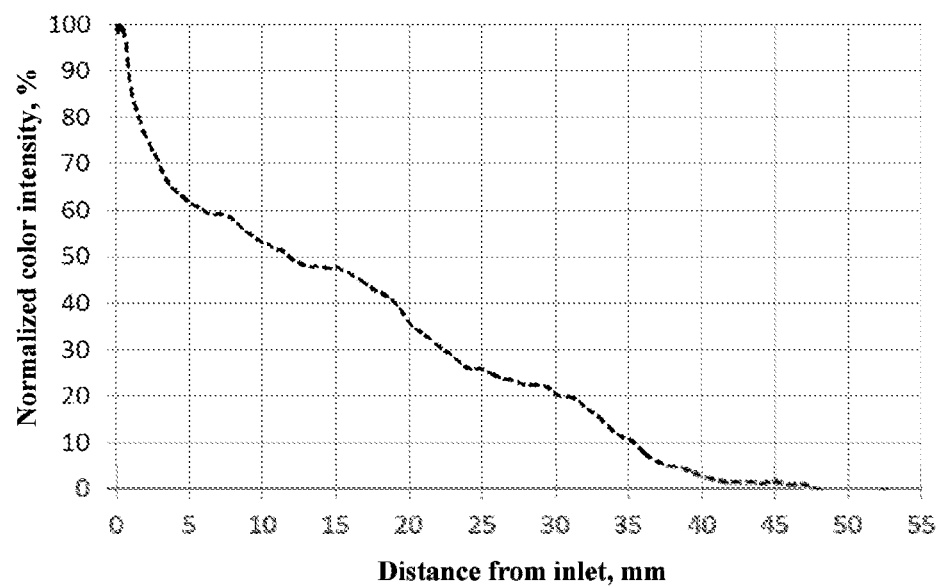
FIG. 4 shows a concentration distribution curve for the bentonite contaminant (a 1% slurry in a 1.8% NaCl solution) along a direction axis of the pumping into Castlegate sandstone.

As an example, a 1% bentonite suspension in a 1.8% NaCl solution was colored with a 1% alcohol solution of brilliant green (1 ml 1% alcohol solution per 1 l of the 1% bentonite suspension in the 1.8% NaCl solution) which corresponds to 0.2 mg-eq (0.1 g) of brilliant green per 100 g of bentonite. The obtained suspension was injected into a sample of Castlegate sandstone (the permeability of 1.8% NaCl solution to 850 mD), having a diameter of 30 mm and a length of 60 mm. The treated rock sample was split along a plane going through a core axis. An image of the split was treated with extraction (by a color and its intensity) of portions comprising the colored bentonite. This made it possible to obtain a distribution of the bentonite contaminant (see FIG. 3 that shows the penetration zone and distribution of the bentonite contaminant (the 1% slurry in the 1.8% NaCl solution) in Castlegate sandstone (the core: 30 mm in diameter, 60 mm in length), the split along the sample diameter along the core axis), and to calculate its concentration profile along the core axis (see FIG. 4 that shows a concentration distribution curve for the bentonite contaminant (a 1% slurry in a 1.8% NaCl solution) along the direction axis of the injection into Castlegate sandstone (the core: 30 mm in diameter, 60 mm in length), said curve having been drawn on the basis of the brilliant green pigment intensity distribution).

The invention claimed is:

1. A method for determining a distribution and a profile of solid particles in a rock core, the method comprising:
    coloring at least one solid particle having a negative-charged surface with a cationic dye;
    injecting a suspension of a drilling mud through the rock core, the drilling mud comprising the at least one colored solid particle having the negative-charged surface;
    splitting the rock core; and
    determining a distribution and a profile of the colored solid particles with the negative-charged surface in the rock core based on a distribution and an intensity of the cationic dye held in a crystalline structure or on a surface of the at least one solid particle or both by processing an image of the obtained split.

2. The method of claim 1, wherein the solid particles with the negative-charged surface are colored by adding the cationic dye to the drilling mud suspension.

3. The method of claim 2, wherein additionally the solid particles with the negative-charged surface are colored with another cationic dye; and
    injecting a suspension of the drilling mud comprising the solid particles with the negative-charged surface colored by the other cationic dye through the rock core.

4. The method of claim 1, wherein different solid particles with the negative-charged surface are colored with different cationic dyes.

5. The method of claim 1, wherein the cationic dye is selected from the group consisting of: fuchsine, methylene blue and brilliant green.

6. The method of claim 1, wherein bentonite is used as the solid particles with the negative-charged surface.

7. The method of claim 1, wherein after the injection of the suspension of the drilling mud a formation fluid is injected through the core from a core end face opposite to an end face from which the suspension of the drilling mud was injected.

8. The method of claim 1, wherein another cationic dye, different from that used to color the solid particles with the negative-charged surface, is applied onto a surface of the rock core.

\* \* \* \* \*